United States Patent [19]

Nowak

[11] Patent Number: 4,932,943
[45] Date of Patent: Jun. 12, 1990

[54] NASOGASTRIC TUBE HOLDING DEVICE

[75] Inventor: George M. Nowak, Lake Villa, Ill.

[73] Assignee: Hollister Incorporated, Libertyville, Ill.

[21] Appl. No.: 197,826

[22] Filed: May 23, 1988

[51] Int. Cl.⁵ .............................................. A61M 25/00
[52] U.S. Cl. .................................... 604/180; 604/178; 128/DIG. 26
[58] Field of Search ........................ 604/174, 177–180; 128/DIG. 26

[56]  References Cited

U.S. PATENT DOCUMENTS

| | | |
|---|---|---|
| 2,831,487 | 4/1958 | Tafilaw . |
| 2,908,269 | 10/1959 | Cheng .......................... 128/DIG. 26 |
| 3,046,989 | 7/1962 | Hill . |
| 3,146,778 | 9/1964 | Krawiec . |
| 3,977,407 | 8/1976 | Coleman et al. . |
| 4,120,304 | 10/1978 | Moor . |
| 4,142,527 | 3/1979 | Garcia . |
| 4,282,871 | 8/1981 | Chodorow et al. . |
| 4,360,025 | 11/1982 | Edwards ...................... 128/DIG. 26 |
| 4,480,639 | 11/1984 | Peterson et al. . |
| 4,516,293 | 5/1985 | Beran .......................... 128/DIG. 26 |
| 4,738,662 | 4/1988 | Kalt et al. ............................ 604/180 |
| 4,774,944 | 10/1988 | Mischinski .................. 128/DIG. 26 |
| 4,804,374 | 2/1989 | Laskody .............................. 604/180 |

*Primary Examiner*—Stephen C. Pellegrino
*Assistant Examiner*—Ralph Lewis
*Attorney, Agent, or Firm*—Tilton, Fallon, Lungmus

[57]  ABSTRACT

A nasogastric tube holding device having an adhesive pad and a pair of clamping jaws pivotally supported along one edge of the pad. The jaws include adjustable latching means for securely but releasably holding nasogastric tubes in wide ranges of size and durometer and for permitting adjustment in the positions of such tubes as desired.

15 Claims, 3 Drawing Sheets

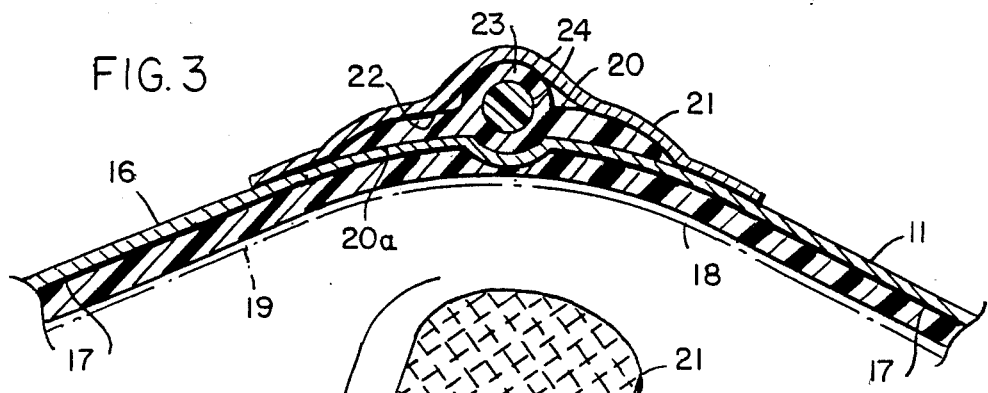
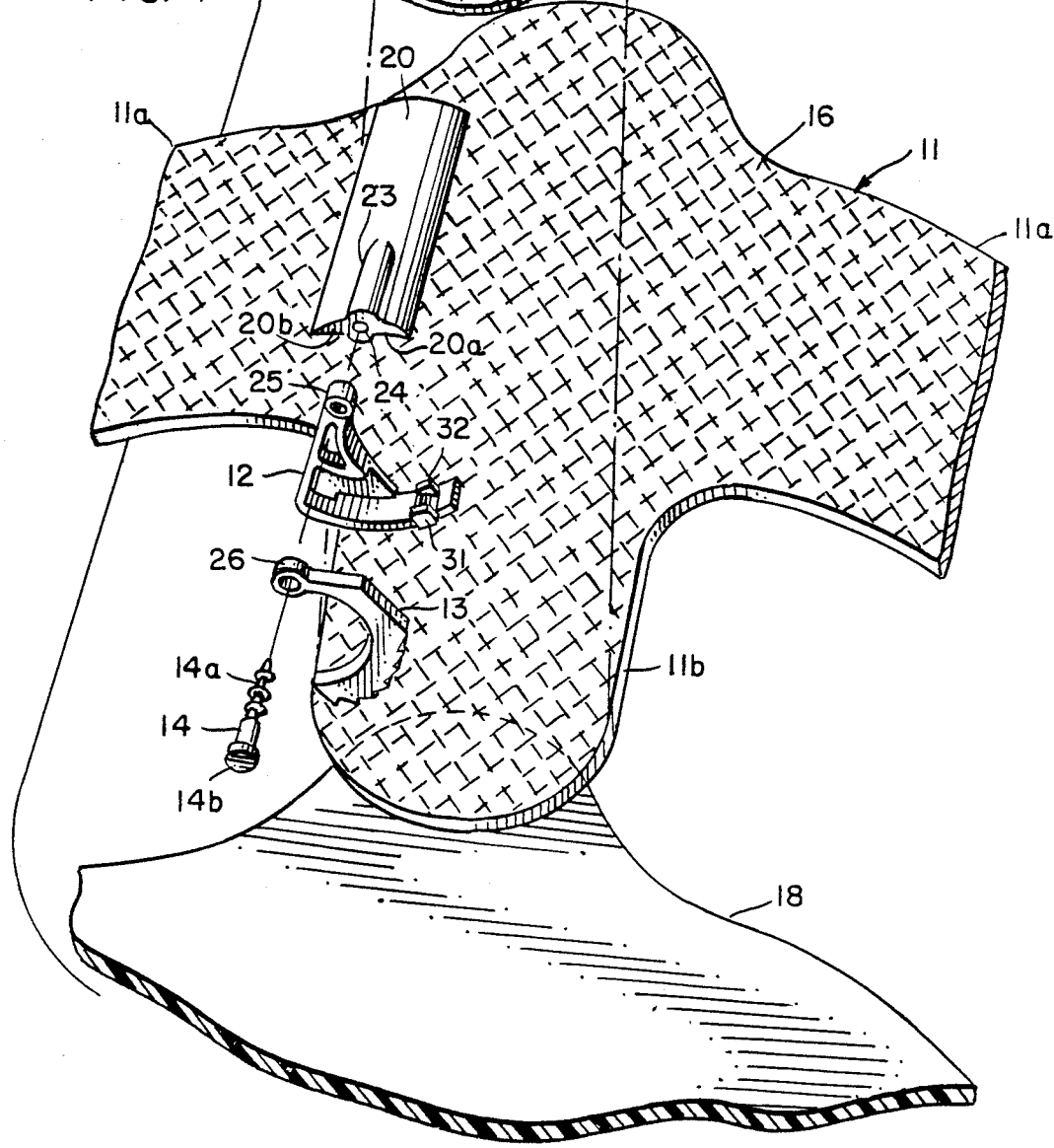

NASOGASTRIC TUBE HOLDING DEVICE

BACKGROUND AND SUMMARY

Nasogastric tubes are available in a variety of sizes and materials, the selection for any given patient depending on factors such as the size or age of the patient, the expected duration of the intubation, and the precise purpose for such intubation. In general, nasogastric tubes are commonly available in sizes ranging between 6 to 18 French (about 0.080 to 0.240 inches), and the materials from which they are formed may be relatively soft or of low durometer such as, for example, silicone rubber, or considerably stiffer or of higher durometer, such as polyvinyl chloride. The stiffer materials are needed when such a tube is to be used for aspirating purposes, since the material must be capable of resisting collapse when suction is applied, whereas the softer materials are frequently used for feeding purposes, especially where relatively long-term use is anticipated.

While various types of nasogastric tube holders have been disclosed in the prior art, such devices are all believed to have significant shortcomings. Quite typically, such a device includes an adhesive patch or a strap for attachment to the patient, coupled with holding means for securing the nasogastric tube to the patch or strap. The holding means often takes the form of adhesive tape (U.S. Pat. Nos. 4,142,527, 3,046,989, 3,146,778, 3,977,407) but such tape, although capable of accommodating tubes of different size, is not readily detachable from the tubes when removal or adjustment is required. Mechanical holding means (U.S. Pat. Nos. 4,831,487, 4,120,304) generally involve slotted U-shaped members formed of relatively rigid plastic and, while slidable adjustment or detachment may be readily accomplished, such holders cannot connect to tubes of different size nor are they adjustable to insure secure attachment to tubes of the same size but different degrees of softness Also, with mechanical holders carried by an elongated strap (e.g., 4,120,304) as well as with devices utilizing tape or sutures as the holding means (3,146,778), a pistoning action of the tube may occur and result in considerable discomfort and possible injury to the patient. Clamping devices capable of detachably receiving nasogastric tubes of different size are known (4,282,871, 4,480,639), but such clamps are of the spring-action type and, therefore, any force sufficient to overcome the bias of the springs may result in release of the tubes and, again, possibly serious risks for the patients.

Accordingly, one aspect of this invention lies in providing a device having a pair of clamping jaws that are readily adjustable for holding nasogastric tubes of different size and durometer, may be securely latched together and maintained in such latched condition by positive action rather than spring action, and are nevertheless separable when disconnection from or adjustment of a nasogastric tube is required. The clamping jaws are pivotally mounted immediately adjacent the edge of a flexible pad that is adhesively secured over a wearer's nose when the device is in use, and the close proximity of the jaws to the end of the patient's nose, and the relative stiffness of that portion of the pad overlying the ridge of the nose, eliminates or greatly reduces the likelihood of pistoning action. Although the clamping jaws securely hold a nasogastric tube in place, effectively resisting forces tending to move the tube longitudinally, the clamp may be easily and quickly released by intentional lateral displacement of a flexible latching arm provided by one of the jaws.

Most advantageously, the pad takes the form of a thin layer of soft, porous sheet material such as the soft, non-occlusive tapes commonly used in the medical field. The underside of the sheet or tape is coated with a pressure-sensitive adhesive and, in a preferred embodiment, a layer of skin-barrier material may be secured to that portion of the underside of the tape that extends over the ridge of a wearer's nose. Secured to the upper surface of the tape by an adhesive patch that is preferably formed of the same material as the tape is a mounting plate that gives the pad a desired contour, adds stiffness to the pad along the ridge of the wearer's nose, and provides support for the pivot pin on which the jaws are mounted. By providing the plate with a socket and the pivot pin with a barbed end portion, the clamping arms may be joined to the pad as the final step in the manufacture of the device.

Therefore, the device essentially comprises a flexible, non-occlusive, adhesive pad that is adapted for adhesive attachment to a patient's nose, a pivot pin secured to the pad adjacent one of its edges, and a pair of clamping jaws pivotally supported by the pin for movement between closed and open positions. The jaws are provided with adjustable latching means for selectively and releasably latching the jaws in any of a plurality of closed positions, with the result that nasogastric tubes of different outside diameters and different degrees of softness may be effectively clamped and retained by the jaws. The latching means takes the form of ratchet teeth provided by the jaws, one of the jaws having a series or rack of such teeth, and the other jaw having at least one ratchet tooth selectively engageable with the teeth of the first jaw. The two jaws have arcuate faces disposed in opposition when the jaws are closed, at least one of the arcuate faces including a narrow bearing rib and the other jaw having a bearing surface that directly opposes the rib when the jaws are closed. Because of such construction, closing of the jaws, even about a tube of relatively small size, does not result in a scissoring action nor does it tend to cause a twisting of the nasogastric tube out of parallel relation with the pivot axis of the jaws.

Other features, advantages, and objects of the invention will become apparent from the specification and drawings.

DRAWINGS

FIG. 3 is an enlarged fragmentary cross sectional view taken along line 3—3 of FIG. 2.

FIG. 4 is an exploded fragmentary perspective view showing the parts of the assembly.

DETAILED DESCRIPTION OF PREFERRED EMBODIMENT

Figure 1:
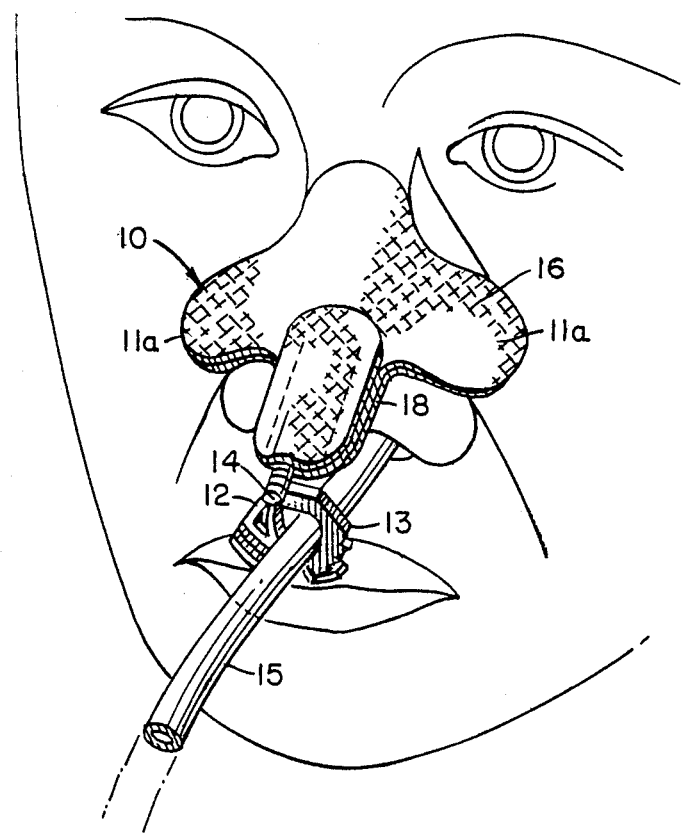
FIG. 1 is a perspective view showing a device of the present invention as it would appear when worn by a patient.

Referring to the drawings, the numeral 10 generally designates a nasogastric tube holder including an adhesive pad 11 and a pair of pivotally-mounted clamping jaws 12 and 13. The jaws are pivotally supported by a pivot pin 14 that is generally coplanar with the adhesive pad 11 and that, as shown most clearly in FIGS. 1 and 2, protrudes from one edge of the pad.

The pad includes a pair of wing portions 11a that are dimensioned and arranged to extend downwardly and outwardly along opposite sides of a wearer's nose and a central portion 11b that extends along the ridge of the nose adjacent to the tip thereof (FIG. 1). While some protrusion of the central portion 11b beyond the tip of the nose is acceptable, such protrusion should be kept to a minimum to avoid the possibility of pistoning action should longitudinal forces be exerted on nasogastric tube 15.

Figure 2:
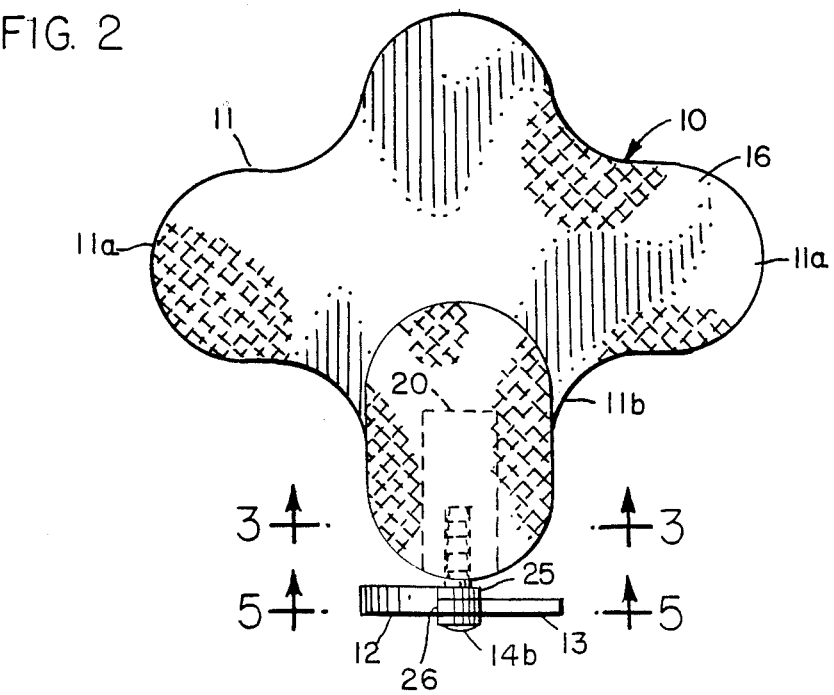
FIG. 2 is a top plan view of the device.

In a preferred embodiment, the pad includes a thin layer 16 of soft, flexible, porous sheet material. A particularly effective material is believed to be the non-woven, non-occlusive sheet material formed of spun-laced polyester marketed by Minnesota Mining and Manufacturing Co., under the designation 3-M tape No. 1776 or by Fasson Tape under the designation MED 5322P. It is to be understood, however, that other materials having similar properties may also be used. Any soft, pliant fabric, whether woven or unwoven, that is sufficiently porous to allow for the passage of water vapor and gases therethrough, may be effectively used. Along the underside of the layer 16 is a layer or coating 17 of pressure-sensitive adhesive such as a typical medical-grade acrylic adhesive as commonly used in the manufacture of adhesive tapes for medical use. If desired, a cushioning layer 18 of a soft, tacky, and deformable skin barrier material (such as karaya or a barrier composition of the type designated as "HOLLIHE-SIVE" by Hollister Incorporated, Libertyville, Ill.) may extend along the underside of central portion 11b (FIGS. 2, 3). Also, as indicated in phantom in FIG. 3, the adhesive undersurface 17 and the barrier layer 18 (if included) would normally be covered with a strippable release layer 19 of paper or other suitable material to protect the tacky adhesive surfaces of layers 17 and 18 until use of the product is desired.

An insert plate 20 is disposed above layer 16 of pad 11 and is held in place by a patch 21 having an adhesive coating 22 along its undersurface. The patch 21 may be formed of the same porous material as layer 16, and coating 22 may be of the same adhesive material as layer 17.

As shown most clearly in FIG. 4, the insert plate 20 is generally rectangular in outline and arcuate in section, with the concave undersurface 20a of the plate facing downwardly and engaging the upper surface of porous layer 16. Because of its cross sectional curvature, the insert plate readily adapts to the curvature along the ridge of a wearer's nose. In addition, the curvature of the flexible plate imposes a curvature in the pad itself, as depicted most clearly in FIG. 3. The upper patch 21 extends over the insert plate and conceals the plate except for the front face 20b that terminates immediately adjacent the front edge of the central portion 11b of the pad. The front portion of the insert plate includes an enlargement 23 in which a forwardly-facing socket or opening 24 is formed. That socket receives and retains the barbed end 14a of pivot pin 14 when the parts are fully assembled.

Figure 5:
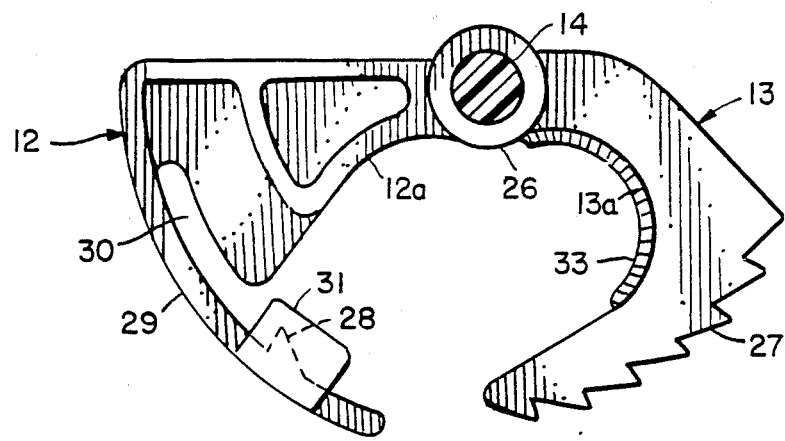
FIG. 5 is an enlarged sectional view taken along line 5—5 of FIG. 2 and showing the jaws in open position.

Clamping jaws 12 and 13 have apertured hubs 25 and 26 that pivotally receive the shank of pin 14. The enlarged head 14b of the pin retains the jaws together upon the pin and in close proximity to the end of insert plate 20 (FIG. 2). The pivotally-mounted jaws may be swung between open positions such as shown in FIG. 5 (the jaws may be spread apart even further than shown in that figure) and the closed position illustrated in FIG. 8.

The jaws are provided with adjustable latching means for selectively and releasably locking those jaws in any of a plurality of closed positions. The latching means takes the form of intermeshing ratchet teeth provided by the respective jaws. Jaw 13 includes a series of teeth 27 disposed at an equal distance from the longitudinal axis of pivot pin 14 and, hence, from the pivot axis of jaws 12 and 13. Jaw 12 has at least one tooth 28 adapted to mate with any of the teeth 27 of jaw 13. Tooth 28 is carried by spring arm portion 29 of jaw 12. A slot 30 allows the arm to flex over a substantial portion of its length, as indicated by arrow 31 in FIG. 8. Normally the arm assumes the raised or latching position depicted in solid lines in FIGS. 5–8 but, when the tip 29a of the arm is urged downwardly (i.e., away from the ratchet teeth 27 of jaw 13) into the lowered position shown in broken lines in FIG. 8, the ratchet teeth are disengaged and the jaws may be shifted into the open positions shown in FIG. 5.

Figure 6:
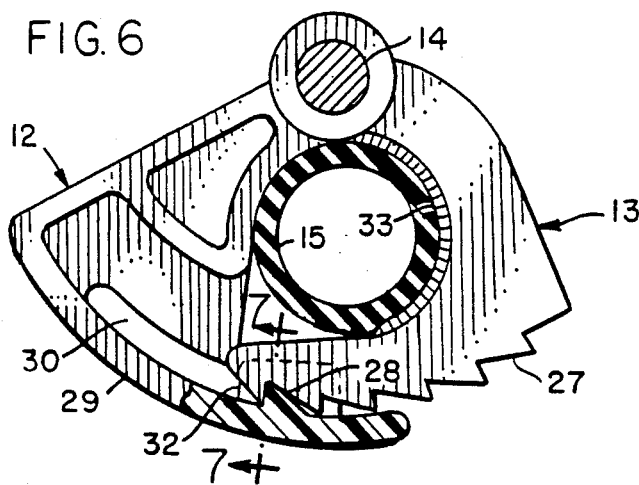
FIG. 6 is a sectional view similar to FIG. 5 but showing the jaws in closed position about a relatively large nasogastric tube.
Figure 7:
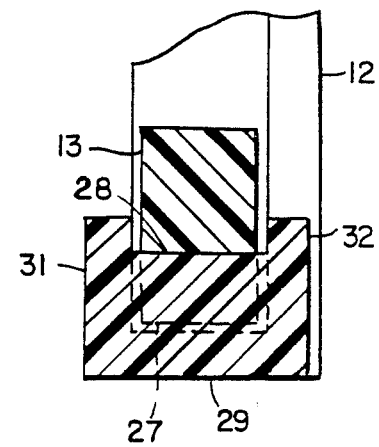
FIG. 7 is a greatly enlarged fragmentary sectional view taken along line 7—7 of FIG. 6.
Figure 8:
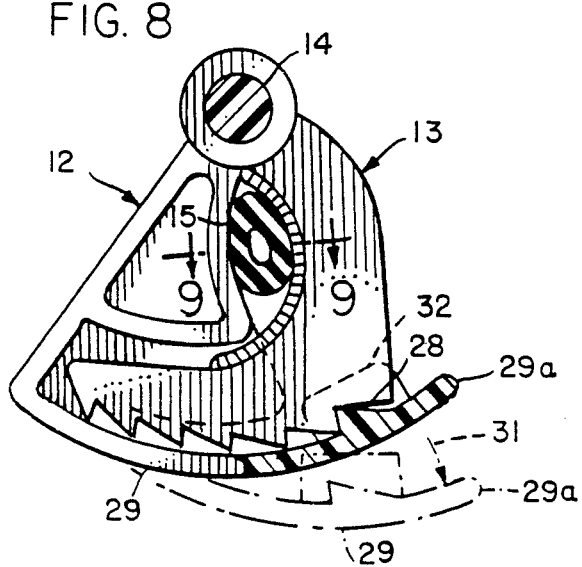
FIG. 8 is a sectional view similar to FIG. 6 but showing the jaws clamped about a relatively small-diameter tube.

Arm portion 29 includes a pair of side flanges 31 and 32 that prevent lateral movement of jaw 13 when the two jaws are latched together as shown in FIGS. 6–8. It will be observed that the side flanges are disposed on opposite sides of tooth 28 and, since the parts are integrally formed, the tooth and flanges are mutually reinforcing and together prevent unlatching of the jaws in response to lateral forces (i.e., forces parallel with pivot pin 14) exerted upon the jaws.

Figure 9:
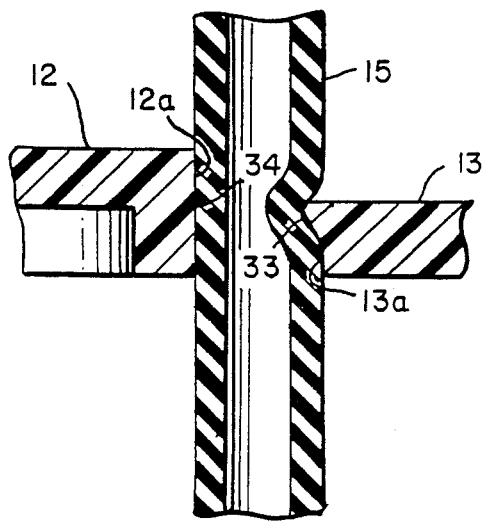
FIG. 9 is a greatly enlarged longitudinal sectional view taken along line 9—9 of FIG. 8.

Jaws 12 and 13 have arcuate inner faces 12a and 13a that oppose each other when the jaws are in closed positions. One of the jaws 13 has a narrow bearing rib 33 that increases the force concentration exerted on a nasogastric tube and increases the security of the clamping action on that tube. It will be noted from FIG. 9 that the opposing jaw 12 has sufficient thickness in its wall section to provide a portion 34 that directly opposes jaw 13 and its rib 33 to prevent a scissoring action when the jaws are urged into clamping engagement with a resilient nasogastric tube.

FIG. 6 illustrates the positions of the jaws when they are closed about a tube of maximum size as, for example, an 18 French tube of approximately 0.240 inches in outside diameter. It will be observed that the last tooth 27 at the tip of jaw 13 engages tooth 28 of jaw 12. FIG. 8 illustrates the relationship of parts when the jaws retain a smaller tube of 6 French (0.080 inches). Over their full range of adjustment, such jaws securely engage and retain the resilient tubing against movement relative to the clamping jaws without reducing the lumen size of the tube more than about 20 percent, and then only with tubes at the smaller end of the size range.

While in the foregoing I have disclosed an embodiment of the invention in considerable detail for purposes of illustration, it will be understood by those skilled in the art that many of these details may be varied without departing from the spirit and scope of the invention.

What is claimed is:

1. A device for holding a nasogastric tube in position, comprising a flexible adhesive pad adapted to be adhesively secured to a patient's nose; a pivot pin secured to said pad adjacent one edge thereof and having an end portion protecting outwardly from said edge; said pin having its longitudinal axis extending generally along the plane of said pad; a pair of clamping jaws pivotally supported by said end portion of said pin for movement of said jaws between closed and open positions; and adjustable latching means provided by said jaws for selectively and releasably latching said jaws in any of a plurality of said closed positions for holding nasogastric tubes of different outside diameters between said clamping jaws.

2. The device of claim 1 in which said jaws have arcuate faces generally disposed in opposition when said jaws are closed for clamping a nasogastric tube therebetween.

3. The device of claim 2 in which the arcuate face of one of said jaws includes a narrow arcuate bearing rib.

4. The device of claim 3 in which the arcuate face of the other of said jaws includes a portion directly opposing said bearing rib of said one jaw when said jaws are closed.

5. A device for holding a nasogastric tube in position, comprising a flexible adhesive pad adapted to be adhesively secured to a patient's nose; a pivot pin secured to said pad adjacent one edge thereof and having an end portion projecting outwardly from said edge; a pair of clamping jaws pivotally supported by said end portion of said pin for movement of said jaws between closed and open positions; and adjustable latching means provided by said jaws for selectively and releasably latching said jaws in any of a plurality of said closed portions for holding nasogastric tubes of different outside diameters between said clamping jaws; said latching means comprising ratchet teeth provided by said jaws.

6. The device of claim 5 in which said ratchet teeth provided by one of said jaws extends in an arcuate series with each tooth of said series equidistant from the axis of said pivot pin; the other of said jaws having at least one ratchet tooth selectively engagable with the ratchet teeth of said series.

7. The device of claim 6 in which said other of said jaws is provided with a flexible arm having a free and portion from which said one tooth projects; said free end portion of said arm being capable of being flexed away from said one jaw when disengagement of the teeth of said jaws is desired.

8. A device for holding a nasogastric tube in position, comprising a flexible adhesive pad adapted to be adhesively secured to a patient's nose; a pivot pin secured to said pad adjacent one edge thereof and having an end portion projecting outwardly from said edge; a pair of clamping jaws pivotally supported by said end portion of said pin for movement of said jaws between closed and positions; and adjustable latching means provided by said jaws for selectively and releasably latching said jaws in any of a plurality of said closed positions for holding nasogastric tubes of different outside diameters between said clamping jaws; and a flexible plate being secured to said pad adjacent said one edge thereof; said plate providing a socket receiving an end portion of said pivot pin opposite from said one end portion thereof.

9. The device of claim 8 in which said opposite end portion of said pin is provided with barb means engaging said plate within said socket for securing said pin and plate together.

10. The device of claim 8 or 9 which said pad comprises a layer of soft, flexible and porous material having a tacky adhesive undersurface for adhering said pad to a wearer.

11. The device of claim 10 in which said plate is secured to an upper surface portion of said layer of porous material.

12. The device of claim 11 in which said plate is secured to said layer of porous material by an adhesive patch overlying said plate and having a peripheral portion projecting beyond said plate and adhesively secured to said upper surface portion of said layer of porous material.

13. The device of claim 12 in which said patch is formed of soft, flexible, porous material.

14. The device of claim 11 in which a layer of soft, tacky, pliable skin barrier is secured to said adhesive undersurface of said layer of porous material beneath said plate.

15. The device of claim 8 in which said plate is elongated and arcuate in cross section.

* * * * *